(12) United States Patent
Seppi et al.

(10) Patent No.: US 7,103,137 B2
(45) Date of Patent: Sep. 5, 2006

(54) RADIATION SCANNING OF OBJECTS FOR CONTRABAND

(75) Inventors: Edward J. Seppi, Portola Valley, CA (US); Marcel Marc, San Jose, CA (US); John Ford, Madison, TN (US)

(73) Assignee: Varian Medical Systems Technology, Inc., Palo Alto, CA (US)

( * ) Notice: Subject to any disclaimer, the term of this patent is extended or adjusted under 35 U.S.C. 154(b) by 0 days.

(21) Appl. No.: 10/202,273

(22) Filed: Jul. 24, 2002

(65) Prior Publication Data

US 2004/0017888 A1    Jan. 29, 2004

(51) Int. Cl.
*G01N 23/00*    (2006.01)

(52) U.S. Cl. ............................................. 378/9; 378/57
(58) Field of Classification Search ................. 378/57, 378/58, 10, 9
See application file for complete search history.

(56) References Cited

U.S. PATENT DOCUMENTS

| | | | |
|---|---|---|---|
| 3,018,374 A | 1/1962 | Pritchett | |
| 3,636,353 A | 1/1972 | Untermyer | |
| RE28,544 E | 9/1975 | Stein et al. | |
| 3,924,132 A | 12/1975 | Koslow | |
| 4,031,545 A | 6/1977 | Stein et al. | |
| 4,149,081 A | 4/1979 | Seppi | |
| 4,196,352 A * | 4/1980 | Berninger et al. ............. | 378/7 |
| 4,229,654 A | 10/1980 | Arya et al. | |
| 4,251,726 A | 2/1981 | Alvarez | |
| 4,352,021 A | 9/1982 | Boyd et al. | |
| 4,357,535 A | 11/1982 | Haas | |
| 4,430,568 A | 2/1984 | Yoshida et al. | |
| 4,521,900 A | 6/1985 | Rand | |
| 4,599,740 A | 7/1986 | Cable | |
| 4,631,741 A | 12/1986 | Rand et al. | |
| 4,671,256 A | 6/1987 | Lemelson | |
| 4,722,096 A | 1/1988 | Dietrich et al. | |
| 4,918,315 A | 4/1990 | Gomberg et al. | |

(Continued)

FOREIGN PATENT DOCUMENTS

WO    WO 96/13839    5/1996

OTHER PUBLICATIONS

McDonald, Marci; "Checkpoint Terror Border Searches Snarl the Free Flow of Goods" U.S. News and World Report, p. 52, Feb. 11, 2002.

(Continued)

*Primary Examiner*—Edward J. Glick
*Assistant Examiner*—Jurie Yun
(74) *Attorney, Agent, or Firm*—Brandon N. Sklar; Kaye Scholer LLP

(57) ABSTRACT

A scanning unit for identifying contraband within objects, such as cargo containers and luggage, moving through the unit along a first path comprises at least one source of a beam of radiation movable across a second path that is transverse to the first path and extends partially around the first path. A stationary detector transverse to the first path also extends partially around the first path, positioned to detect radiation transmitted through the object during scanning. In one example, a plurality of movable X-ray sources are supported by a semi-circular rail perpendicular to the first path and the detector, which may be a detector array is also semi-circular and perpendicular to the path. A fan beam may also be used. Radiographic images may be obtained and/or computed tomography ("CT") images may be reconstructed. The images may be analyzed for contraband. Methods of scanning objects are also disclosed.

95 Claims, 8 Drawing Sheets

U.S. PATENT DOCUMENTS

| | | | | |
|---|---|---|---|---|
| 4,941,162 | A | 7/1990 | Vartsky et al. | |
| 4,956,856 | A | 9/1990 | Harding | |
| 4,987,584 | A | 1/1991 | Doenges | |
| 5,044,002 | A | 8/1991 | Stein | |
| 5,065,418 | A | 11/1991 | Bermbach et al. | |
| 5,076,993 | A | 12/1991 | Sawa et al. | |
| 5,098,640 | A | 3/1992 | Gozani et al. | |
| 5,115,459 | A | 5/1992 | Bertozzi | |
| 5,124,554 | A | 6/1992 | Fowler et al. | |
| 5,153,439 | A | 10/1992 | Gozani et al. | |
| 5,200,626 | A | 4/1993 | Schultz et al. | |
| 5,278,418 | A | 1/1994 | Broadhurst | |
| 5,313,511 | A | 5/1994 | Annis et al. | |
| 5,367,552 | A * | 11/1994 | Peschmann | 378/57 |
| 5,410,156 | A | 4/1995 | Miller | |
| 5,420,905 | A | 5/1995 | Bertozzi | |
| 5,490,218 | A | 2/1996 | Krug et al. | |
| 5,491,734 | A | 2/1996 | Boyd et al. | |
| 5,493,596 | A | 2/1996 | Annis | |
| 5,495,106 | A | 2/1996 | Mastny | |
| 5,524,133 | A | 6/1996 | Neale et al. | |
| 5,557,108 | A | 9/1996 | Tumer | |
| 5,600,303 | A | 2/1997 | Husseiny et al. | |
| 5,600,700 | A | 2/1997 | Krug et al. | |
| 5,611,502 | A | 3/1997 | Edlin et al. | |
| 5,638,420 | A | 6/1997 | Armistead | |
| 5,642,394 | A | 6/1997 | Rothschild | |
| 5,692,028 | A | 11/1997 | Geus et al. | |
| 5,692,029 | A | 11/1997 | Husseiny et al. | |
| 5,696,806 | A | 12/1997 | Grodzins et al. | |
| 5,729,582 | A | 3/1998 | Ham et al. | |
| 5,818,054 | A | 10/1998 | Randers-Pehrson et al. | |
| 5,838,758 | A | 11/1998 | Krug et al. | |
| 5,838,759 | A | 11/1998 | Armistead | |
| 5,841,832 | A | 11/1998 | Mazess et al. | |
| 5,917,880 | A | 6/1999 | Bjorkholm | |
| 5,930,326 | A | 7/1999 | Rothschild et al. | |
| 5,966,422 | A * | 10/1999 | Dafni et al. | 378/9 |
| 5,974,111 | A | 10/1999 | Krug et al. | |
| 6,018,562 | A * | 1/2000 | Willson | 378/9 |
| 6,041,097 | A | 3/2000 | Roos et al. | |
| 6,078,642 | A | 6/2000 | Simanovsky et al. | |
| 6,088,423 | A | 7/2000 | Krug et al. | |
| 6,151,381 | A | 11/2000 | Grodzins et al. | |
| 6,218,943 | B1 | 4/2001 | Ellenbogen | |
| 6,236,709 | B1 * | 5/2001 | Perry et al. | 378/57 |
| 6,249,567 | B1 | 6/2001 | Rothschild et al. | |
| 6,259,762 | B1 | 7/2001 | Pastyr et al. | |
| 6,269,142 | B1 | 7/2001 | Smith | |
| 6,278,115 | B1 | 8/2001 | Annis et al. | |
| 6,292,533 | B1 | 9/2001 | Swift et al. | |
| 6,347,132 | B1 | 2/2002 | Annis | |
| 6,411,674 | B1 | 6/2002 | Oikawa | |
| 6,438,201 | B1 * | 8/2002 | Mazess et al. | 378/56 |
| 6,449,334 | B1 | 9/2002 | Mazess et al. | |
| 6,490,337 | B1 * | 12/2002 | Nagaoka et al. | 378/20 |
| 6,628,745 | B1 * | 9/2003 | Annis et al. | 378/21 |
| 6,687,328 | B1 | 2/2004 | Bavendiek et al. | |
| 6,965,661 | B1 * | 11/2005 | Kojima et al. | 378/4 |

OTHER PUBLICATIONS

Grodzins, Lee; Nuclear Techniques For Finding Chemical Explosives In Airport Luggage; Beam Interactions With Materials and Atoms; May 1991; p. 829-833; vol. B56/57, Part II; Elsevier Science Publishers B.V. (North-Holland); Holland.

* cited by examiner

RADIATION SCANNING OF OBJECTS FOR CONTRABAND

FIELD OF THE INVENTION

Radiation scanning of objects, including large objects such as cargo containers, to identify contraband.

BACKGROUND OF THE INVENTION

Radiation is commonly used in the non-invasive inspection of objects such as luggage, bags, briefcases and the like, to identify hidden contraband at airports and public buildings. The contraband may include hidden guns, knives, explosive devices and illegal drugs, for example. One common inspection system is a line scanner, where the object to be inspected is passed between a stationary source of radiation, such as X-ray radiation, and a stationary detector. The radiation is collimated into a fan beam or a pencil beam. Radiation transmitted through the object is attenuated to varying degrees by the contents of the luggage. The attenuation of the radiation is a function of the density of the materials through which the radiation beam passes. The attenuated radiation is detected and radiographic images of the contents of the object are generated for inspection. The images show the shape, size and varying densities of the contents.

To obtain additional information about the contents of the luggage, detectors may be provided to detect scattered radiation, as described in U.S. Pat. No. 5,642,394, for example. Systems may combine detection of scattered radiation with the detection of transmitted radiation.

Another technique to enhance the information that may be derived about the material composition of the contents of the objects is to scan the object with radiation beams having two different energy levels. A ratio of the attenuation detected at two energy levels is indicative of the atomic numbers of the material through which the radiation beam passes. Dual energy systems enable better detection of plastic materials and illegal drugs.

One disadvantage of radiographic imaging is that all items within the object in the path of the radiation beam are superimposed on the image. If there are many items in the object, it may be difficult to distinguish among them. The identification of dangerous items is thereby hampered. In addition, the orientation and shape of the items within the object could effect whether they can be identified on a radiograph. Thin sheets of explosive materials may also be difficult to identify on a radiograph, particularly if they are oriented perpendicular to the scanning beam.

Computed tomography ("CT") enables the reconstruction of the cross-sectional images of luggage contents, facilitating the identification of the items in the luggage. CT images also provide higher resolution, greater image contrast and greater sensitivity to characteristics of the object being scanned, than radiographs. However, reconstruction of CT images of an object requires a large number of scans of the object at a plurality of angles. Conducting a sufficient number of scans for CT reconstruction is time consuming. Depending on the system used, CT imaging of an entire piece of luggage may be too slow for practical use in screening luggage in airports, for example.

In U.S. Pat. No. 5,367,552 ("the '552 patent"), a source of X-ray radiation is provided on one side of an inner surface of a rotating module and a detector array is provided on the opposite side. Luggage is moved through the module incrementally. The module rotates to scan the luggage at a plurality of angles, at each incremental position. The inspection speed may be increased by pre-screening with a line-scan. Then, only suspicious regions identified by the pre-screening step are subjected to CT imaging.

U.S. Pat. No. 6,078,642 ("the '642 patent) discloses a CT scanning system for luggage where data processing techniques are used to speed the inspection rate. As in the '552 patent, an X-ray source and a detector array are disposed on opposing sides of a rotating module. The source may emit a pyramidal cone beam of radiation and the detector array may be 2-dimensional. The module rotates as a piece of luggage is continuously moved through the module, providing helical volumetric CT scanning. CT scanning is said to be provided of the entire piece of luggage, without requiring pre-scanning. The source may emit an X-ray beam of two different energy distributions, as well.

While the smuggling of contraband such as guns and explosives onto planes in carry-on bags and in luggage has been a well known, ongoing concern, a less publicized but also serious threat is the smuggling of contraband across borders and by boat in large cargo containers. Only 2%–10% of the 17 million cargo containers brought to the United States by boat are inspected. "Checkpoint terror", U.S. News and World Report, Feb. 11, 2002, p. 52.

Standard cargo containers are typically 20–50 feet long (6.1–15.2 meters), 8 feet high (2.4 meters) and 6–9 feet wide (1.8–2.7 meters). Air cargo containers, which are used to contain a plurality of pieces of luggage or other cargo to be stored in the body of an airplane, may range in size (length, height, width) from about 35×21×21 inches (0.89×0.53× 0.53 meters) up to about 240×118×96 inches (6.1×3.0×2.4 meters). Large collections of objects, such as many pieces of luggage, may also be supported on a pallet. Pallets, which may have supporting side walls, may be of comparable sizes as cargo containers and use of the term cargo container will generally encompass pallets, as well.

In contrast to the cargo container size ranges, typical airport scanning systems for carry-on bags have tunnel entrances up to about 0.40×0.60 meters. Scanning systems for checked luggage have travel openings that are only slightly larger. Since only bags that fit through the tunnel may be inspected, such systems cannot be used to inspect cargo containers. The low energies used in typical X-ray luggage and bag scanners, described above, are also too low to penetrate through the much larger cargo containers. In addition, many such systems are too slow to economically inspect larger objects, such as cargo containers.

U.S. Pat. No. 6,292,533 B1 discloses a mobile X-ray inspection system for large objects, such as a cargo container carried by a vehicle, that uses an X-ray source of 450 kV. The source is supported on a truck and a pencil beam is generated to vertically scan the vehicle. Detectors, also supported on the truck or a boom extending from the truck, are provided to detect radiation transmitted through and scattered by the contents of the object. In use, a vehicle to be inspected parks alongside the scanning unit on the truck.

The source and detectors are moved horizontally by a translation system within the truck to horizontally scan the vehicle. While having sufficient penetration, use of a pencil beam may be too slow to efficiently scan cargo containers. The scan motion is said to be "exceedingly slow" (⅓–⅙ of a mile per hour).

U.S. Pat. No. 5,917,880 discloses an X-ray inspection apparatus that may be used to inspect cargo containers, that uses X-ray radiation of about 8 MeV, collimated into a vertical fan beam to scan a truck carrying the cargo. A first detector array is aligned with the fan beam to detect radiation transmitted through the truck. A second detector array is provided to detect radiation forward scattered through the truck. The truck is moved through the vertical fan beam. Data from both detectors is used to determine the average atomic number of the attenuating material in the truck to identify the material content in the truck. Images indicative of the material content are then prepared. Data provided by the first detector array is also used to form radiographs of the truck. While faster than a pencil beam, a fan beam may still be too slow to efficiently scan large objects at a reasonable rate.

In U.S. Pat. No. 5,638,420, large containers are inspected by a system on a movable frame. A source of a fan beam, a cone beam or a pencil beam of X-ray radiation, such as a linear accelerator with an accelerating potential in the MV range, is mounted on one side of the frame. A detector array is mounted on an opposing side of the frame. The frame may be self-propelled and advances across the length of the container. Radiographic images are generated for analysis by an operator.

Radiographic images of large objects such as cargo containers suffer from the same problems described above with respect to radiographic images of smaller objects such as luggage. U.S. Pat. No. 5,524,133 discloses scanning systems for large objects such as freight in a container or on a vehicle. In one embodiment, two stationary sources of X-ray radiation are provided, each emitting a beam that is collimated into a fan beam. The sources facing adjacent sides of the freight and the fan beams are perpendicular to each other. A stationary detector array is located opposite each source, on opposite sides of the freight, to receive radiation transmitted through the freight. In addition, X-ray radiation of two different energies are emitted by each source. One energy is significantly higher than the other. For example, energies of 1 MeV and 5 or 6 MeV may be used. A ratio of the mean number of X-rays detected at each energy level by the detector array as a whole for each slice or by the individual detectors of the array is determined and compared to a look up table to identify a mean atomic number corresponding to the ratio. The material content of the freight is thereby determined. Three dimensional images based on the ratios of mean atomic number may be reconstructed from the data collected by both detector arrays. The patent states that while the images are coarse, they enable the shapes of certain items to be determined. In combination with the determination of the mean atomic number of the materials in those items, suspicious items may be eliminated or flagged for further inspection.

While three dimensional images based on radiographs are an improvement over radiographs themselves, the high resolution, improved image contrast and the ability to distinguish small differences in characteristics of items within in an object that are provided by CT scanning would be advantageous in the inspection of cargo containers. The CT scanning units used in airports for luggage and the like discussed above are not readily scaleable to the large sizes required to scan cargo containers. For example, to accommodate a cargo container, the rotating modules of the '552 patent or the '642 patent would need to be greatly enlarged. Such large rotating units, carrying both the sources and the detectors, would be very expensive and would be difficult to operate and maintain.

In medical CT scanning, there is a configuration referred to as fourth generation, wherein a source of X-ray radiation rotates completely around a patient in a path of a circle within a larger, stationary circular detector array. Fourth generation CT scanners have been found to be an improvement over earlier generations of scanners where both the source and the detector arrays are moved. Scanning times are shorter and the construction of the scanner is simpler. The arrangements of sources and detectors in medical CT scanners are described in more detail in Seeram, Euclid, *Computed Tomography: Physical Principles, Clinical Applications, and Quality Control*, Second Edition, W. B. Saunders Company, (2001), pp. 10, 77–81. While only the source is moved completely around the patient, enlargement of such a system to accommodate large objects such as cargo containers would still be difficult.

Despite the various designs for the inspection of large objects such as cargo containers disclosed in the patents discussed above and in other references, much of the inspection of cargo containers is done manually, if at all. "Checkpoint terror", U.S. News and World Report, Feb. 11, 2002, p. 52. Practical, efficient, non-intrusive radiation scanners for the inspection of large objects, such as cargo containers, are still needed. The ability to perform CT imaging of large objects is needed, as well.

SUMMARY OF THE INVENTION

In accordance with one embodiment of the present invention, a scanning unit for examining contents of an object is disclosed comprising a first path through the scanning unit to transport an object and at least one source of a beam of radiation. The at least one source of a beam of radiation is movable across a second path transverse to the first path. The second path is within a first region extending partially around the first path. A stationary detector is provided in a second region extending partially around the first path. The detector array is positioned to detect radiation transmitted through the object during scanning. The at least one source of a beam of radiation may be a source of X-ray radiation, for example. A transport system may be provided to convey the object through the scanning unit, along the first path. The object may be a cargo container, for example.

A plurality of sources of radiation may be provided. The scanning unit may further comprise a semi-circular rail perpendicular to the first path, to support the sources. The sources may be movable with respect to the rail, about the semi-circle. The detector may comprise a detector array comprising a semi-circular row of detectors perpendicular to the first path and lying on an imaginary circle having a center within the object when the object is in a position for scanning. The detector array may comprise a plurality of two dimensional detectors. At least one energy sensitive detector may be provided.

A processor may be electrically coupled to the detector array. The processor may be programmed to reconstruct computed tomography images based on data received from the detector array.

In accordance with another embodiment of the invention, a scanning unit for examining the contents of an object is disclosed comprising a first path through the scanning unit to transport an object and a plurality of sources of X-ray radiation on a first side of the path. Each source provides a cone beam of X-ray radiation and is mechanically movable across a second path transverse to the first path. The second path is within a first region extending partially around the first path. A detector is provided in a second region extending partially around the first path, positioned to detect each of the radiation beams emitted by the plurality of sources after each beam passes through the object during scanning. The plurality of sources may be supported by a semi-circular rail supported by the scanning unit perpendicular to the first path. The semi-circular rail lies on an imaginary circle having a center within the object when the object is in position for scanning. The rail supports the plurality of sources and the sources are movable in a semi-circle about the rail. In addition, the detector array is semi-circular, is perpendicular to the path, and lies on an imaginary circle having a center within the object when the object is in position for scanning. The detector array may be stationary. The object may be a cargo container, for example.

At least one of the sources may emit radiation having a first energy distribution and at least one of the sources may emit radiation having a second energy distribution different than the first energy distribution. Alternatively, one or more of the sources may selectively emit radiation having different energy distributions. A second, energy sensitive, detector, may be provided such that the first detector is between the second detector and the plurality of sources.

A processor may be electrically coupled to the first and second detector, programmed to reconstruct computed tomography images based on data received from the first detector, to reconstruct energy based images based on data received from the second detector and to fuse the images based on data from the first detector array with the images based on the data received from the second detector. The second detector may be an energy sensitive detector.

In accordance with another embodiment of the invention, a method of examining contents of a cargo container is disclosed comprising scanning at least a portion of the cargo container with a radiation beam at a plurality of angles, detecting radiation transmitted through the cargo container and processing data based on the detected radiation to form computed tomographic images of at least the portion of the cargo container. The radiation beam may be a cone beam. A plurality of sources of radiation may be provided to scan the cargo container. The radiation beam (or beams) may be X-ray radiation. Multiple energy distributions may be used. The entire cargo container may be scanned first to generate radiographs of the container. Suspicious regions may then be scanned at a plurality of angles and computed tomography images reconstructed of the suspicious regions. The cargo containers may have a height and width greater than 5 feet (1.5 meters).

A method of examining contents of an object is also disclosed, comprising moving the object along a first path and moving at least one source of a radiation beam along a second path transverse to the first path to scan the object. The second path is within a first region extending partially around the first path. The method further comprises detecting radiation transmitted through the object by a stationary detector array. The stationary detector array lies within a second region extending partially around the first path.

A method of examining the contents of an object is also disclosed comprising moving the object in a first direction and irradiating the object with a plurality of cone beams of X-ray radiation. Each cone beam is emitted from a respective one of a plurality of sources of X-ray radiation. The X-ray sources are arranged in a semi-circle lying on a first imaginary circle with a center within the cargo. The semi-circle is transverse to the first direction. The plurality of X-ray sources are mechanically moved about the semi-circle to irradiate the cargo with each cone beam at a plurality of angles, wherein the semi-circle lies on the first imaginary circle. Radiation transmitted through the object is detected with by a semi-circular, stationary detector array of modules of two dimensional detectors. The semi-circle lies on a second imaginary circle with a center within the object, lying in a same plane as the first imaginary circle. The detected radiation is analyzed.

A scanning unit for examining a target is also disclosed, comprising a first path through the scanning unit to move the target and a plurality of sources of beams of radiation. The plurality of sources are movable across a second path transverse to the first path. A detector is positioned to detect radiation transmitted through a target during scanning.

As used herein, the term "cargo container" encompasses pallets.

DESCRIPTION OF THE PREFERRED EMBODIMENTS

Figure 1:
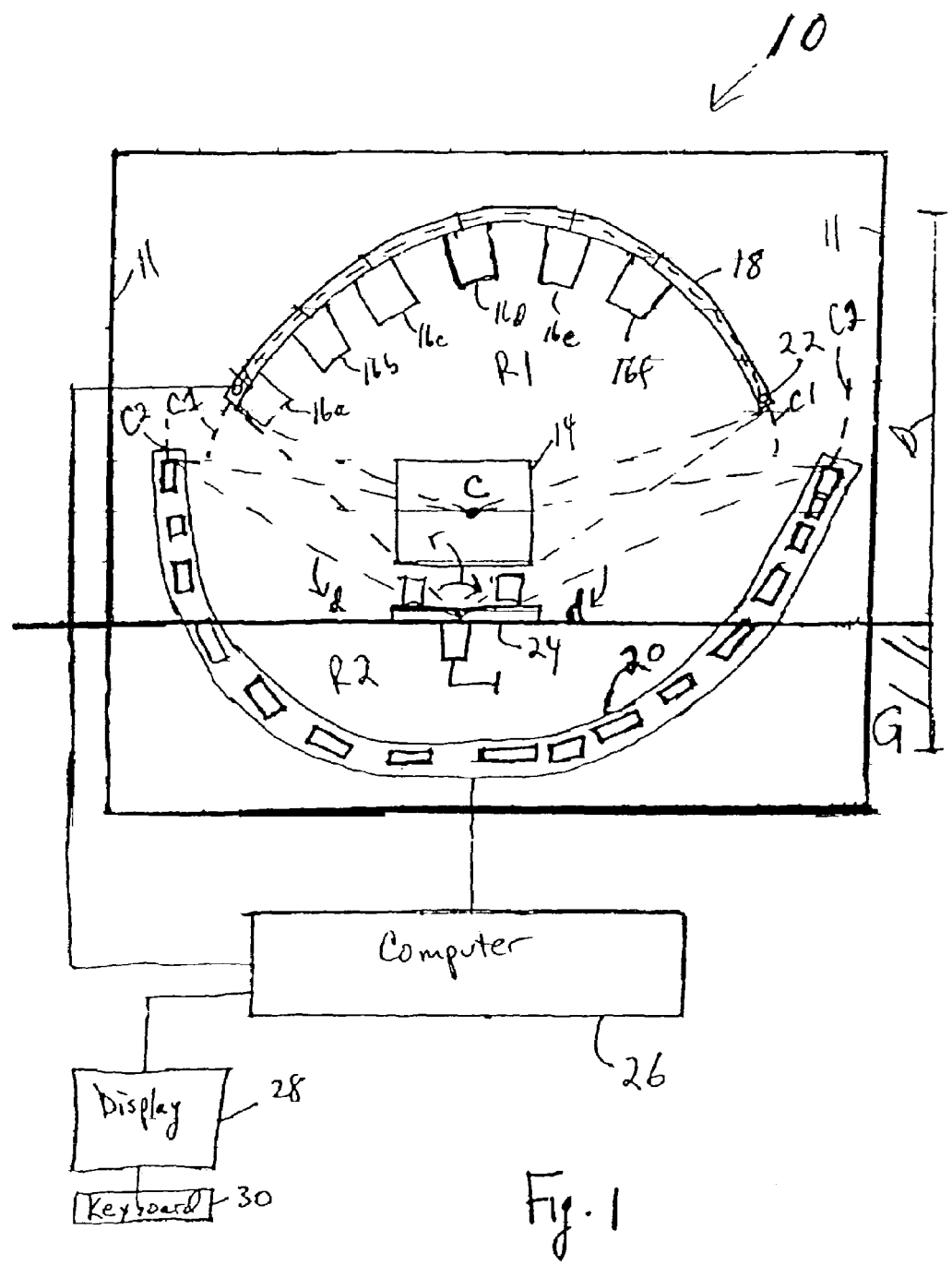
FIG. 1 is a front schematic view of an interior of a cargo scanning unit in accordance with one embodiment of the invention.
Figure 2:
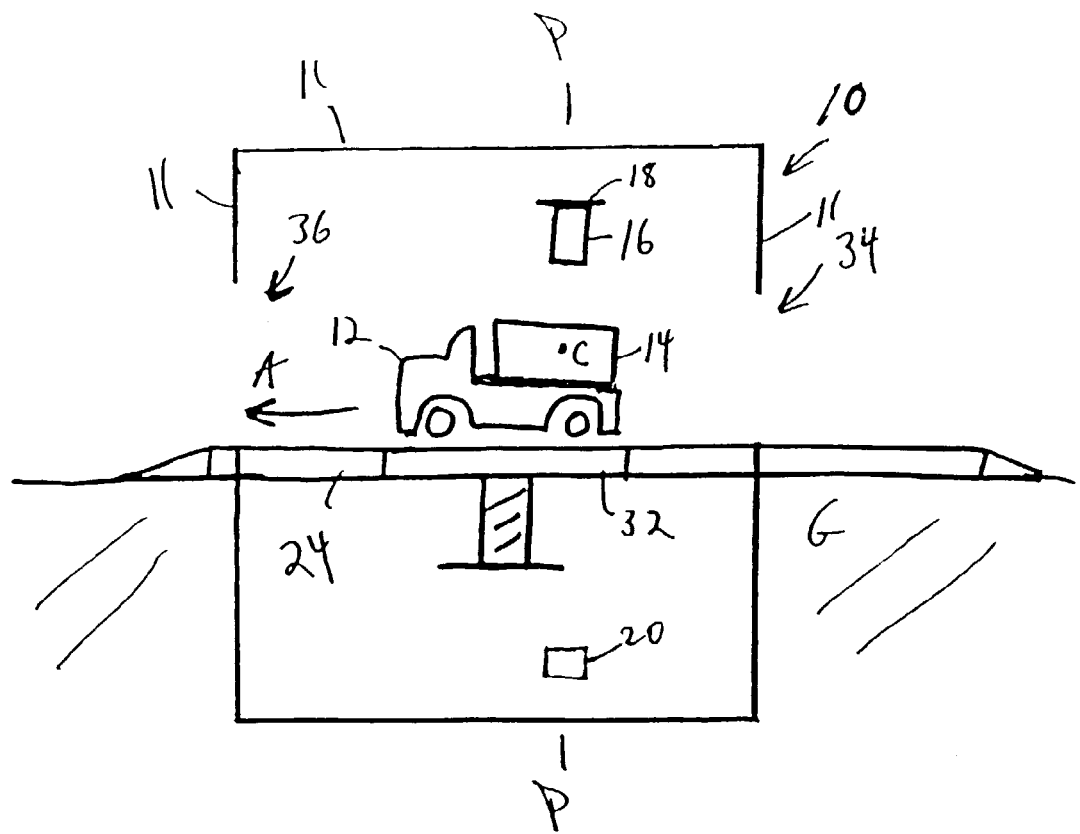
FIG. 2 is a side, interior view of the scanning unit of FIG. 1, showing the truck being moved through the unit, along the direction of arrow "A"

FIG. 1 is a front schematic view of an interior of a cargo scanning unit 10 for inspecting objects for contraband, such as explosive devices and materials, in accordance with one embodiment of the invention. FIG. 2 is a side schematic view of the center of the interior of the cargo scanning unit 10. The objects can be small objects, such as luggage and bags, or large objects, such as cargo containers. The scanning unit 10 comprises shielded walls 11. In FIG. 1, a truck 12 carrying a cargo container 14 is shown moving through the scanning unit 10, out of the page, along a first path. In FIG. 2, the direction of the first path is indicated by arrow "A".

Figure 3:
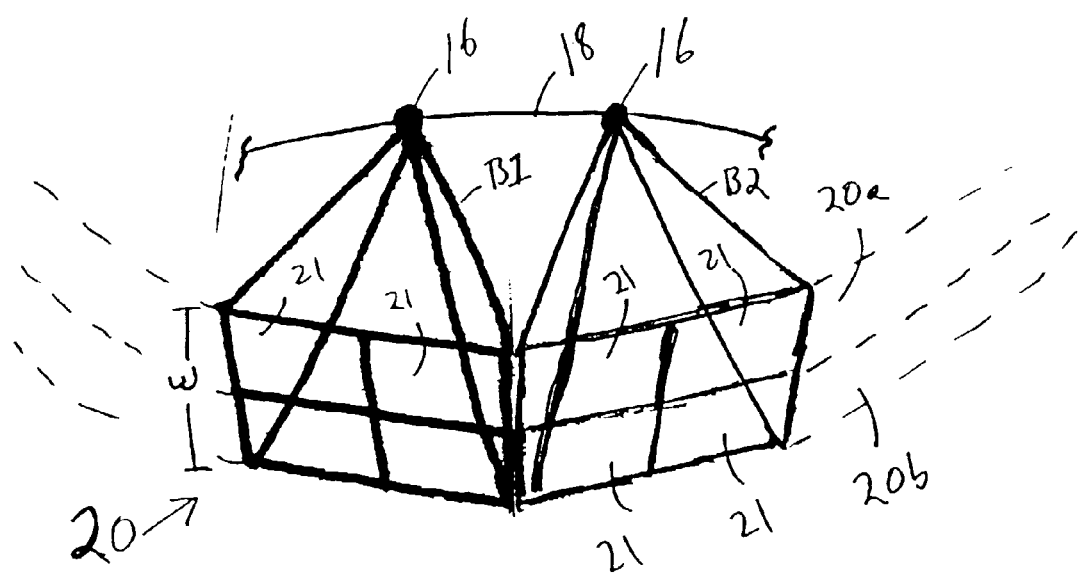
FIG. 3 is a schematic representation of two asymmetric cone beams emitted by adjacent X-ray sources, illuminating a portion of a detector array.

In this embodiment, the scanning unit 10 comprises six X-ray sources 16a–16f, a rail 18 supporting each of the X-ray sources 16a–16f and a detector 20. The detector 20 may be a detector array comprising a plurality of detector modules 21, as shown in FIG. 3, for example. The rail 18 and the detector array 20 lie along the same plane "P", identified in FIG. 2, to detect radiation emitted by the sources 16a–16f after passing through the cargo container 13. The plane P is transverse to the first direction A along the first path. In this embodiment, the plane P is perpendicular to the first direction A and to the first path.

A conveying system 22 is provided to move the X-ray sources 16 along the rail 18 and/or to move the rail.

The X-ray sources 16a–16f and/or the rail are moved within a region R1 extending only partially around the first path A. Therefore, the sources 16a–16f are not moved completely around the path A (or the cargo container 14). Similarly, the detector array 20 lies within a region R2 extending only partially around the first path A. The detector array 20 does not extend completely around the cargo container 14, either. In (the embodiment of FIG. 1, the Regions R1 and R2 are wholly separate, although there may be some overlap, if desired.

In the embodiment of FIG. 1, the rail 18 is semi-circular and lies on a first imaginary circle C1 with a center that is at or close to the center C of the cargo. Similarly, in this embodiment, the detector array 20 is also semi-circular and lies on a second imaginary circle C2 with a center at or close to the center C of the cargo. While in the embodiment of FIG. 1, the first and second imaginary circles are not the same, they may be. The first and second imaginary circles both lie in the same plane P. The detector array 20 may be straight or have other shapes, as well. The extents of the arcs of the semi-circular rail 18 and detector array 20 depend on the characteristics of the beams emitted by the sources 16a–16f, as discussed further below.

The sources 16a–16f and the detector array 20 are arranged and spaced a sufficient distance "D" so that the truck 12 and cargo container 14 may pass between them. For a typical cargo container 14 of 20×8×8 feet (6.1×2.4×2.4 meters) supported by a typical truck 12, a distance D of about 25 feet (7.62 meters) may be provided.

A transport system 24, such as a moving belt connected to the truck 12 or a track along the path A, may be provided to move the truck through the cargo scanning unit 10 along the path A. The belt or track may be driven by one or more motors (not shown).

The cargo container 14 need not be supported by the track 12. The cargo container 14, or other such object to be inspected, may be directly supported and conveyed by the transport system 24. The motor driven belt or track may also be used to directly convey the cargo container 14. Mechanically driven rollers may also be used.

The detector array 20 detects X-rays transmitted through the cargo container 14. The detector array 20 is electrically connected to a processor 26, such as a computer, which reconstructs the data output by the detector array 20 into images, as discussed further below. Analog-to-digital converting devices and other electronic components are provided as required. The computer 26 is connected to a display 28 that displays the reconstructed images. The computer 26 may store the reconstructed images in a database, along with identifying information about each truck 12 or cargo container 14, such as the license plate, and other useful information, such as the date that the truck is scanned. The operator of the scanning unit 10 can enter the relevant information though a keyboard 30 or the information can be scanned or otherwise entered automatically. The computer 26 is also connected to the X-ray sources 16 to control their operation, to the conveyor system 22 to control movement of the sources 16 and/or the rail 18 and to the transport system 24. Multiple processors or computers may be used, as well.

The transport system 24 may include a vertical platform 32, shown in FIG. 2, to lift or lower the truck 12 as necessary to position the center C of the cargo container 14 at or near the center of the imaginary circles of the rail 18 and the detector array 20, under the control of the computer 26. An entrance 34 and exit 36 of the scanning unit 10 are shown, as well.

The conveyor system 22 moves all the sources 16 simultaneously, in one direction and then in the opposite direction, to enable scanning of the entire volume of the cargo container 14 at a plurality of angles. The conveyor system 24 may comprise a motor driven closed chain (not shown) supported by the rail 18. The X-ray sources 16 may be supported by the rail 18 and moved by the chain by gears, for example, coupled to the motor. The motor may be controlled by the computer 26 to move the chains first in one direction, then in the opposite direction, continuously or in discrete intervals. Depending on the length of the rail 18, the rail itself can be moved, instead of or in addition to moving the sources 16, by providing an appropriate supporting and conveying system for the rail. The conveying system 22 for the rail 18 may be a mechanically driven track or mechanically driven rollers, as well.

The X-ray source 16 may be a source of Bremstrahlung radiation, for example. To examine cargo containers having a width greater than about 5 feet (1.5 meters) by a scanning unit 10 in accordance with the embodiment of FIG. 1, the X-ray source may generate radiation having an energy distribution with an average energy greater than about 1 MeV. The X-ray source 16 may generate radiation having an energy distribution with an average energy greater than about 6 MeV, for example. The X-ray source 16 may be a linear accelerator, such as a Linatron® Linear Accelerator ("Linatron®"), having an accelerating potential in a range of about 6 MV or more, available from Varian Medical Systems, Inc., Palo Alto, Calif. ("Varian"), for example. In the Varian Linatron®, 360 pulses are output per second. The Varian Linatron® has an opening angle of about 20–30 degrees, for example. Other X-ray sources may be used as well, such as electrostatic accelerators, microtrons and betatrons, for example. X-ray tubes may also be used, particularly for objects having a width less than about 5 feet (1.5 meters).

If Varian Linatrons® are used as the sources 16 in the configuration of FIG. 1, six sources may be provided, equidistantly spaced on the semi-circular rail 18, to illuminate a pie-shaped region of about 120 degrees of the cargo container 14. The emissions of each source 16 are synchronized with the detector or detectors of the detector array 20 that each source illuminates, by the computer 26. The emissions of the sources 16 may or may not be synchronized with each other to emit pulses simultaneously. The sources may emit radiation at angles up to about 180 degrees, which can be collimated to any desired shape, such as a cone or fan beam. The radiation beam can be emitted from a point, as in a linear accelerator, along a line or from a two-dimensional area.

One or more collimators (not shown) may be provided between each of the X-ray sources 16 and the cargo container 14 to collimate the X-ray beam from each source 16 into a cone beam. The cone beam may be an asymmetric rectangular cone, for example. Two adjacent asymmetric rectangular cone beams B1, B2 are shown in FIG. 3. The use of rectangular cone beams avoids exposure of the cargo to excessive radiation that is not used in imaging the cargo container. It also minimizes scattered radiation that may be detected, improving image quality. A circular cone beam could be used but data collected from portions of the cone beam proximate the boundary of the circle would typically be discarded. Other shaped cone beams could be used, as well.

The cone beam need not be a mathematical cone; it may be an arbitrarily shaped cone. Here, "cone beam" refers to an X-ray beam having longitudinal and lateral dimensions to illuminate a two dimensional detector, as described further, below. A cone beam is used in this embodiment because a cone beam can uniformly scan a larger volume of the cargo container per scan, as compared to a fan beam or a pencil beam, decreasing the time required to scan the entire cargo container 14.

Collimators (not shown) may also be provided between the cargo container 14 and the detector array 20 to block scattered radiation from reaching the detectors 21 of the detector array.

When the X-ray radiation is in the form of a cone beam, the detector array 20 may comprise one or more rows of two dimensional detector modules to detect X-ray transmission through the cargo container 14. In FIG. 3, two rows 20a, 20b of detector modules 21 are shown. Each X-ray source 16, shown schematically as a point source on the rail 18, is aimed at a different detector module or modules 21, of the detector array 21, as shown. In FIG. 3, each cone beam B is aimed at a rectangular group of four detector modules. The detector modules 21 are shown enlarged and the cargo container 14 is not shown in FIG. 3, for ease of illustration. Each two-dimensional detector module 21 comprises a plurality of rows and columns of detector elements, such as photosensitive elements, in a housing. The components of the modules, which are known in the art, are not shown. The photosensitive elements may be photodiodes, for example. If a fan beam is used, a single row of one-dimensional detectors (comprising a single row of detector elements) may be used.

The scanning unit 10 may be used to obtain radiographic images or computed tomography ("CT") images. In order to obtain a complete data set for CT reconstruction, either the sources 16a–16f should be moved across an arc or the detector array 20 should extend over an arc, equal to 180° plus the lateral arc of the emitted X-ray beams. For example, if the lateral arc of the beam is about 30°, the arc of the movement of the sources 16a–16f or the arc of the detector array 20 should be about 210°. The arc of the other component should then be about 180°. Alternatively, the arc of both may be about 200°.

The longitudinal or axial width of each cone beam emitted by each source 16a–16f at the detector array 20 may approximately correspond to the width "W" of the detector array, as shown in FIG. 3. The lateral length of each cone beam depends on the number of sources and the lateral length of the detector array 20. In FIG. 3, each cone beam is shown illuminating a lateral length "L" of the detector array 20 comprising two detectors. The lateral lengths of the cone beams may be adjusted so that the adjacent cone beams overlap portions of the detector array 20, to ensure that all the detectors 21 are illuminated.

To simplify analysis of detected signals and reconstruction of images, in one embodiment, only the sources 16a–16f that project X-ray beams that do not overlap on the same detector 21 of the detector array 20 are on at the same time. For example, only one of the sources 16a–16f may be on at a time. Data acquisition may be increased by turning multiple sources on concurrently. Where the lateral length of each cone beam is adjusted so that adjacent beams overlap on the detector array 20, the pairs of sources 16a and 16d, 16b and 16e and 16c and 16f may be on at the same time, for example. For even faster data acquisition, the sources 16a, 16c and 16e may be on at the same time and the sources 16b, 16d and 16f may also be on at the same time. The groups of sources may be cycled on in succession as the sources 16a–16f are moved across the rail 18, under the control of the computer 26. Data from detector modules 21 that are not aligned with a source which is on may be rejected, unless information from scattered radiation is desired.

Figure 4:
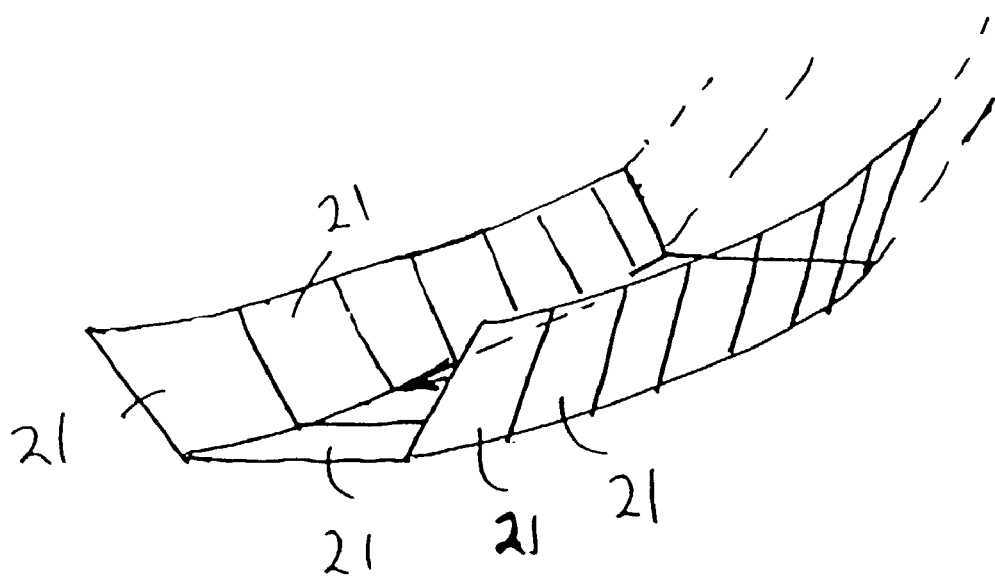
FIG. 4 is a perspective view of a semi-circular trough shaped detector array.
Figure 5:
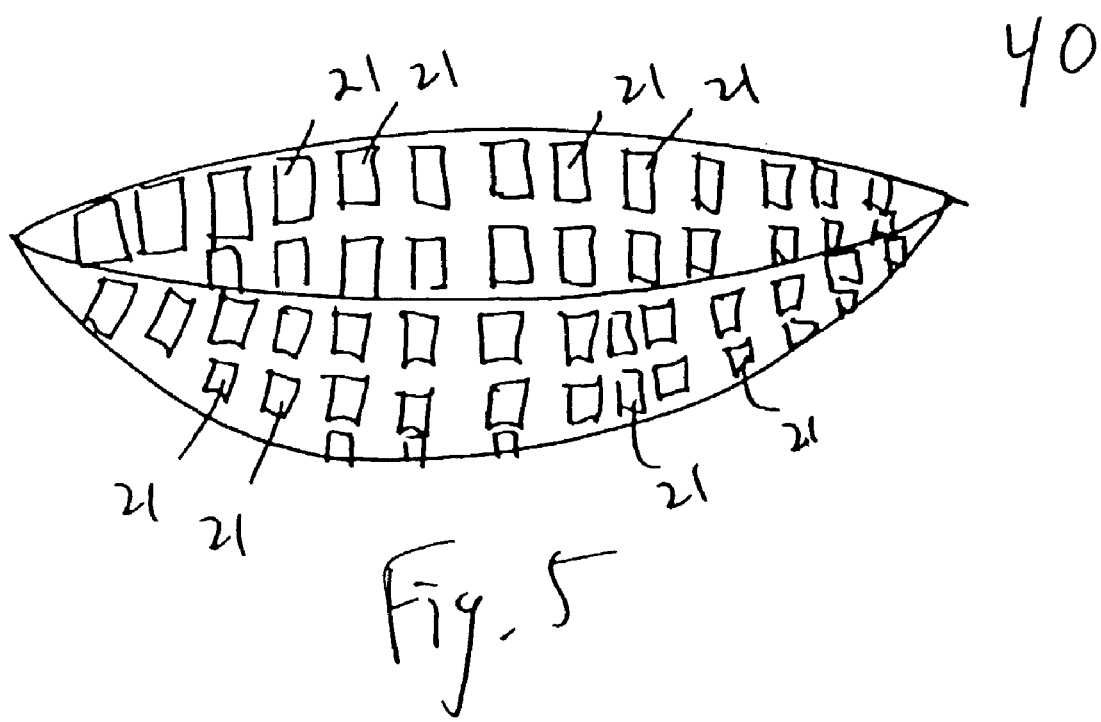
FIG. 5 is a perspective view of a dish shaped detector array.

The detector array 20 may also be shaped like a semi-circular trough 38, as shown in FIG. 4, where three rows of detector modules 21 are provided. The detector array 20 may also have a dish shaped configuration 40, as shown in FIG. 5, for example. The dish shaped detector array 40 may comprise 30×15 rows of detector modules 21, and be shaped like an oval. The oval may extend over a sphere of 180 degrees×90 degrees, for example. The detector array 20 may be a flat, as well. The preprocessing and reconstruction algorithm can correct for the use of a flat detector array.

The spatial detector modules 21 may be amorphous Silicon ("aSi") detectors, for example. Each detector module 21 may be a two dimensional detector, with a width of at least about 20–30 cm, for example. The pixel size may be up to 0.5 cm., for example. The detector module 21 may be a 40 cm×30 cm aSi detector available from Varian, for example under the tradename PaxScan™ 4030, for example. The detectors may be coupled to signal processing circuitry comprising a preamplifier stage with dynamically controllable signal gain, as described in U.S. Ser. No. 09/978,727, assigned to the assignee of the present invention and incorporated by reference, herein. Each detector module 21 may be placed end to end, as shown in FIG. 1.

In one example, to scan a cargo container 14 with dimensions of 20×8×8 feet (6.1×2.4×2.4 meters), carried by a truck 12, thirty-five (35) detector modules 21 each having dimensions of 40 cm×30 cm, may be arranged in a semi-circle extending over an arc d of 210 degrees to form a detector array 20 having a width W of 30 cm and having an arc length of 14 meters. The beams from each of the six X-ray source 16 may be collimated into a cone beam having a width W of about 30 cm and a length of at least about 233 cm (1400 cm/6). Each cone beam may have a length of up to about 350 cm, for example, to illuminate one detector module 21 and up to about half of the adjacent detector modules or regions of the detector array 20 to ensure that all the detector modules 21 are illuminated. Each cone beam may extend laterally over an arc of about 30 degrees and longitudinally over an arc of about 2 degrees to about 15 degrees, dependent on the size of the detector array 20.

In this embodiment, the X-ray sources 16, the rail 18 and the conveyor system 24 are in the upper portion of the scanning unit 10 and the detector array 20 is in the lower portion, as shown in FIG. 1 and FIG. 2. The detector array 20 may be placed in and supported, in whole or in part by, a semi-circular hole in the ground G beneath the transport system 24, as shown in FIG. 1, to provide a narrow, compact structure for the scanning unit. In such a configuration, the ground absorbs much of the radiation, decreasing the amount of shielding required. A radiation dump is not required. The walls 11 above the ground G are appropriately shielded to absorb scattered radiation, as is known in the art. The positions of the detector array 20 and the sources 16 may be reversed and appropriate additional shielding and a radiation dump provided as necessary.

Figure 6:
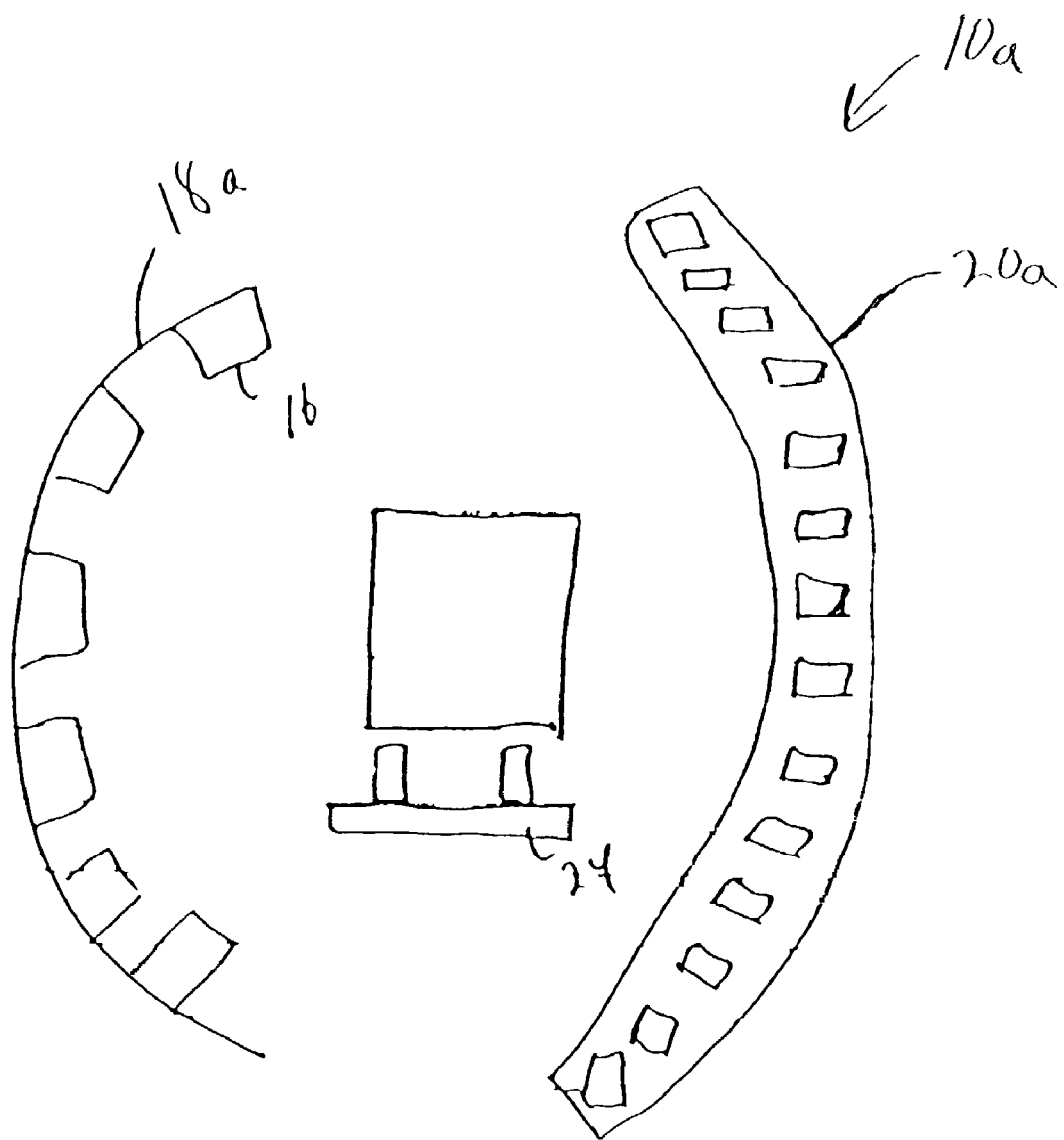
FIG. 6 is a front view of another cargo scanning unit in accordance with an embodiment of the invention, wherein the X-ray sources are on one side of the path traversed by a truck carrying a cargo container and the detectors are on the other side.
Figure 7:
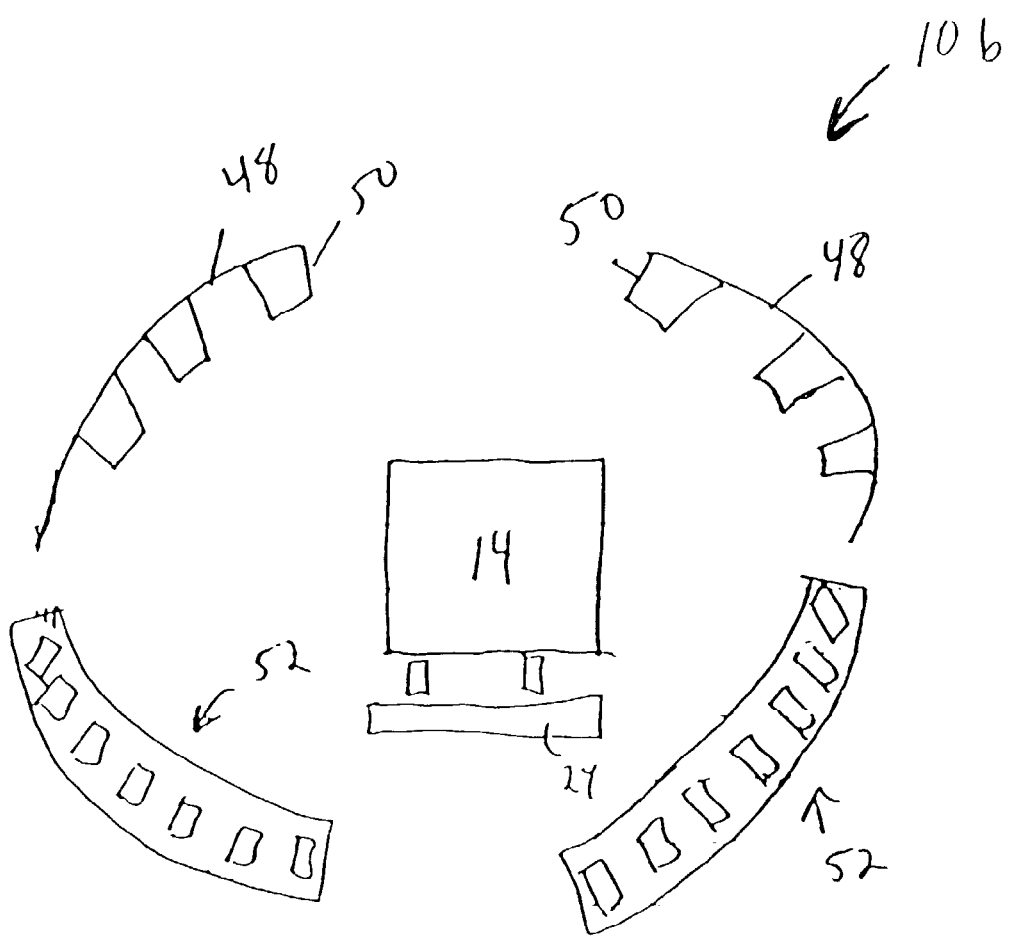
FIG. 7 is a top view of another cargo scanning unit in accordance with an embodiment of the invention, wherein sources and detectors are provided on both sides of the path traversed by a truck carrying a cargo container.

Alternative configurations are possible. FIG. 6 is a front view of a cargo scanning unit 10a, wherein a rail 18a supporting X-ray sources 16 is on one side of the path A traversed by the truck 12 carrying the cargo container 14 and the detector array 20a is on the other side. Shorter rails 48 supporting half of the X-ray sources 50 and shorter detector arrays 52 may also be provided on opposite sides of the cargo container 14 to be scanned, as well, as shown in the front view of a scanning unit 10b in FIG. 7.

Returning to FIG. 1, in use, a truck 12 carrying a cargo container 14 or cargo to be examined is transported through the scanning unit by the transport system 24 at a speed about 0.10 feet per second. The X-ray sources 16 and/or the rail 18 are advanced in a continuous motion across an arc of about 210 degrees in about 10 seconds. X-ray cone beams are transmitted through the cargo container 14 by each of the sources 16. Radiographs of the cargo container 14 are taken at each position of each source 16.

A sufficient number of radiographs may be taken at uniformly spaced angular positions of the sources 16 to perform computed tomography ("CT"). CT may be performed with from about 50 to about 2000 projections per imaging volume where each projection is at a slightly different angle. It is believed that 420–720 projections will provide good results. The imaging volume is the section of the cargo container 14 (and optionally the truck 12) that is scanned in a single sweep of the sources 16a–16f across the rail 18. Images are derived as each source 16a–16f is moved continuously around the rail 18, while the truck 12 is being moved through the scanning unit 10. Data may be collected as the sources 16a–16f are moved every 0.5 degrees, for example. Cone beam reconstruction algorithms, such as a Feltkamp algorithm, may be used to reconstruct axial cross-sectional images of the cargo, as is known in the art.

As discussed above, in order to obtain a complete data set for CT reconstruction, where the cone beam has a lateral arc of about 30 degrees, either the sources 16a–16f should be moved across an arc or the detector array 20 should extend over an arc, equal to about 210 degrees. The arc of the other component should then be 180°. Alternatively, the arc of both may be about 200°.

In cone beam CT systems having a single source and a single detector, an equal number of rays are transmitted from the source to a detector element through each voxel of the object being scanned and the rays have a uniform angular distribution. This data is used by the cone beam reconstruction algorithm to reconstruct an image. In a multi-source cone beam CT system, however, an equal number of rays are not transmitted through each, voxel. In addition, the angular distribution of the rays is only approximately uniform. A pre-processing algorithm may therefore be used to select, weight and process the raw data to compensate for the deviations, so the data may be used in the reconstruction algorithm.

The pre-processing algorithm may also compensate for other aspects of the geometry and configuration of the system 10. For example, ideally, the distance from each source 16 to the detector module 21 of the detector array 20 upon which that source aims its cone beam, is as close to a constant distance as possible. Since each detector module 21 is flat, however, the distance will not be constant in this configuration. The pre-processing algorithm may compensate for the deviation in distance. The pre-processing algorithm may also correct for the space between adjacent detector modules 21 in the detector array 20. As mentioned above, if the cone beams overlap on the detector array 20, corrections are required to properly select and weight the collected data. For example, data collected from portions of the detector array where beams overlap may be summed and averaged. These and other required corrections may be derived based on techniques known in the art for cone beam reconstruction where a single source is used.

One scan by each source 16a–16f may produce about 30 cross-sectional images over 15 centimeters of axial length. Each scan may require about 10 seconds. It may take about 5–10 minutes to conduct CT scanning of an entire cargo container having width and length of about 15 feet×20 feet, for example. A spatial resolution as good as a few millimeters may be obtained. The cargo container 14 may be exposed to a nominally acceptable dose levels, such as 50 Rads, for example.

To increase the scanning rate, a pre-scanning test may be conducted on the cargo to identify suspicious regions of the cargo container 14. CT scanning may then be conducted on the suspicious portions. Trucks carrying cargo without suspicious regions may be cleared more quickly. Trucks with suspicious regions may also be scanned more quickly, since CT scanning is only performed on the suspicious regions.

For example, the scanning unit of FIG. 1 can perform a line scan of the cargo. The X-ray sources 16 are centered over the cargo container 14 by the conveying system 22. Once centered, they need not be moved. The detector array 20 acts as a line detector. Radiographs of the cargo container 14 are reconstructed as the truck 12 passes through the cargo scanning unit 10 at a much higher rate. Radiographs of the entire cargo container 14 may be performed in less than one minute.

Two line scans may be performed along orthogonal scanning directions. The first line scan may be conducted with the sources 16 at one extreme position on the rail 18, such as the leftmost position, as shown in FIG. 1. Then the sources are moved to the opposite extreme position on the rail 18, in this example their rightmost position. The second line scan may then be performed. Additional scans may be conducted with the sources at intermediate positions between the two extremes, as well. Alternatively, the two scans may be performed with the first and last sources 16a, 16f, simultaneously.

The radiographs may be inspected visually or analyzed by the computer 26 to identify suspicious regions based on the shape, size and density of objects in the radiographs. If suspicious regions are identified, then the transport system 24 can be reversed and the X-ray sources 16 moved to conduct CT scanning of the suspicious regions as the cargo container 14 is moved back through the scanning unit 10, for more detailed, three dimensional views of the suspicious regions of the cargo.

Other pre-screening techniques may be used, as well. For example, more rapid scanning may be conducted by moving the sources 16a–16f across the rail 18 as the truck 12 is moved along the path A, and taking less than 300 projections. Taking 100 projections, for example, could be about 5 times faster than taking 500. The cone beam reconstruction algorithm may be used to reconstruct the data. The resulting images may be sufficient for an operator or a computer to identify suspicious regions for more detailed examination. As above, CT may then be conducted on the suspicious regions.

Scattered radiation resulting from pencil beam scanning may also be used in pre-scanning. A collimator may be moved in front of each source to define the pencil beam. Operation of the sources 16a–16f is cycled. One source may be on at a time or sources transmitting beams that do not overlap on the detector array 20 may be on at the same time. Data from detector modules 21 aligned with each transmitted beam may be rejected, so that only scattered radiation is processed. Scanning may be conducted quickly. As above, the resulting images may be sufficient for an operator or a computer to identify suspicious regions for more detailed examination and CT scanning may then be conducted on any suspicious regions.

A pencil probe beam may also be used instead of or along with cone beam (or fan beam) scanning of suspicious regions, identified in pre-screening. The sources 16a–16f may be moved along the rail as the truck 12 is moved by the conveying system 24 to enable the pencil beam or beams to scan the suspicious region from a plurality of angles. Pencil beams are particularly advantageous in scanning small objects.

Scattered radiation need not only be used in pre-scanning. Additional information that may contribute to the identification of contraband within the cargo container 14 may be obtained by detecting radiation scattered by the contents of the container. Additional detectors (not shown) may be provided between the sources 16a–16f and the cargo container 14 to detect back scattered radiation. Alternatively or in addition to the back scatter detectors, additional detectors may be provided at the sides of the cargo container 14 to detect side scattered radiation. The detector array 20 of FIG. 1 can also be used to detect scattered radiation by scanning the cargo container 14 with one source 16 at a time. Radiation transmitted through the cargo container 14 would be detected by the detector or detectors 21 upon which the cone beam is aimed. The other detectors 21 of the detector array 20 will detect scattered radiation.

Additional information useful in identifying contraband may also be obtained by selectively detecting transmitted energy in different energy ranges. Filters (not shown) may be selectively provided in front of the detector array 20 to improve the energy sensitivity of the detector array 20 for a particular energy range. For example, the filters may be configured to block radiation transmitted through the cargo below a certain threshold. An example of a detector that is sensitive over a broad energy range and may be used in the present invention is described in U.S. Ser. No. 10/013,199, filed on Nov. 2, 2002, assigned to the assignee of the present invention and incorporated by reference, herein. Scintillation based detectors comprising photo-multipliers, semiconductor based detectors and gas ionization based detectors sensitive to particular energy ranges are commercially available.

As is known in the art, the interaction of X-ray radiation with different materials, including contraband such as explosives, is dependent on the energy of the X-ray radiation. Additional information useful in identifying contraband may therefore also be obtained by scanning the cargo with two or more different energy distributions having different average energies. The detector array 20 shown in FIG. 1 may be used to detect radiation transmitted through the cargo container 14 at each of the energy distributions. One of the energy distributions may be one with an average energy in which the primary interaction of the X-ray radiation with the cargo is Compton scattering. The other energy distributions may have progressively higher average energies that will cause progressively more pair production and less Compton scattering.

For example, two energy distributions may be provided by X-ray sources with accelerating potentials of 6 MV and 18 MV or higher, respectively. At 6 MV, the X-ray radiation will cause Compton scattering. There is not much pair production. At 18 MV or higher, more pair production is induced. Compton scattering takes place as well.

Different X-ray sources emitting X-ray radiation with different average energies may be used, requiring double the number of sources in the configuration of FIG. 1. Alternatively, each source 16a–16f may be configured to selectively emit X-ray radiation at two or more different energy distributions. Linear accelerators that can emit X-ray radiation at two or more different energy distributions are described in U.S. Pat. No. 6,366,021 B1, U.S. Pat. No. 4,382,208 and U.S. Pat. No. 4,400,650, for example, which are assigned to the assignee of the present invention and are incorporated by reference, herein. The energy distribution of the X-ray beam may be rapidly changed, under the control of the computer 26, in order to scan at both energy distributions when the sources 16 are at each scanning location.

Figure 8:
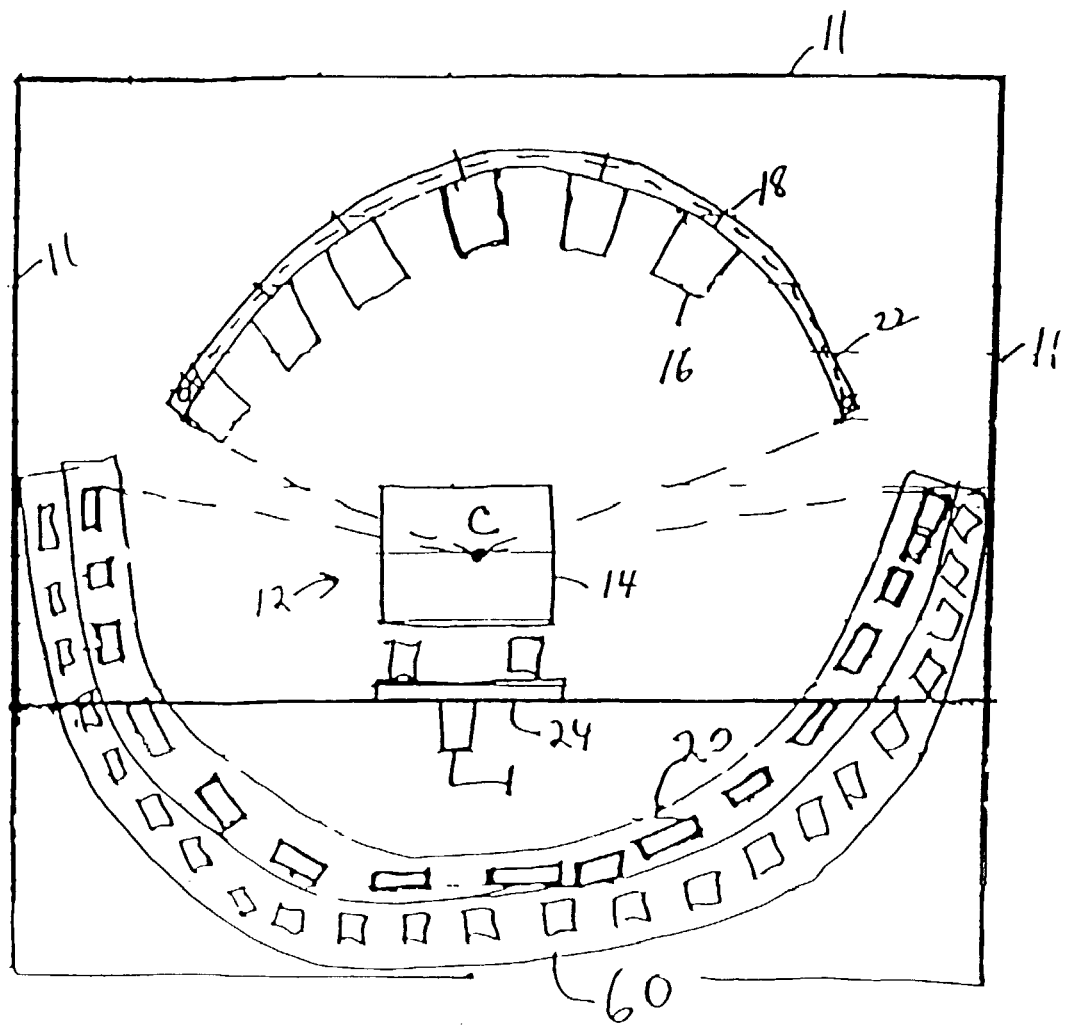
FIG. 8 is a schematic representation of a configuration of a cargo scanning unit including a plurality of X-ray sources that can emit X-ray radiation having more than one energy distribution and an energy sensitive detector array.

As mentioned above, the detector array 20 of FIG. 1 may comprise spatial detectors that detect the radiation transmitted through the cargo container 14 at each energy distribution. Alternatively, energy sensitive detectors may be provided. FIG. 8 is a schematic representation of a configuration of a cargo scanning unit 10c including a plurality of X-ray sources 16 under the control of the computer 26 (not shown in this view) that can emit X-ray radiation having more than one energy distribution. Elements common to the configuration of FIG. 1 are commonly numbered. A second detector array 60 is provided, comprising one or more rows of two dimensional energy sensitive detectors, behind the first detector array 20. The second detector array 60 is responsive to the energy of the X-ray energy transmitted through the cargo container 14 and through the first detector array 20. A sufficient amount of X-ray energy will pass through the first detector array 20 to be detected by the second detector array 60. (While spaces are shown between the detectors 21 and the detector array in FIG. 1 and FIG. 8, the adjacent detectors 21 may be in contact.) Instead of providing a separate energy sensitive detector array 60, two dimensional energy sensitive detectors may also be provided among the two dimensional detectors of the first detector array 20. Filters may be provided between the detector arrays to remove radiation below a certain threshold, to improve the sensitivity of the every sensitive detector array to higher energies, if desired.

Radiographs may be generated, as described above. CT images may also be reconstructed from a sufficient number of radiographs, as well. The energy distribution with the higher average energy may be used to generate the radiographs and CT images.

The detectors 61 of the second detector 60 array may each comprise a scintillator coupled to a photomultiplier tube, for example, as is known in the art. X-ray photons impinging upon the scintillator cause the emission of light photons energies proportional to the energy of the X-ray photons. The light photons are detected by the photomultiplier tube, whose output is proportional to the energy of the detected light photons. Pulse Height Analysis ("PHA") may be used to analyze the data from the energy sensitive detectors. The scintillator may be a cesium iodide, sodium iodide, calcium tungstate, or bismuth germanate scintillator, for example.

Whether only the single detector array 20, as in FIG. 1, or an energy sensitive detector array 60 is also provided, images may be prepared based on data collected at both average energies. Two data points are available at each voxel, each one derived from scanning with a respective energy distribution. The data point derived from scanning at the lower average energy is primarily based on the effects of Compton scattering, which is dependent on the atomic number Z of the material (or materials) in the voxel. The data point derived from scanning at the higher average energy is based on pair production, which is dependant on $Z^2$, as well as Compton scattering. If additional average energies are also used, more data is available that may provide further information about the contents of the cargo container 14. While some of the information is correlated to the information obtained through the use of two energies, the additional information may still be statistically significant. Image contrast may be improved, as well.

Images may be reconstructed based on the scans at each energy level. The images may be compared visually or by the computer 26. The values in all or some of the voxels of the cargo container at each average energy may also be compared or processed to derive information indicative of the material content of the cargo in the voxel. For example, a ratio of the two data points at each voxel yields a value dependent on the average Z and average $Z^2$ of the material in the voxel. The ratio may be compared by the computer 26 to a database corresponding ratios with materials to identify the material in the voxel. U.S. Pat. No. 4,149,081, for example, discusses the analysis and viewing of data sets derived from different energy levels, in a manner generally applicable here. U.S. Pat. No. 4,194,081 is assigned to the assignee of the present invention and is incorporated by reference herein.

Both data points are also dependent on the density of the material in the voxel. The total density of the material may be useful in identifying contraband (explosives, nuclear material and illegal drugs, for example). However, the density of the material may be readily modified by mixing in fillers of different densities, without changing the deleterious characteristics of the contraband. The change in density may make a dangerous explosive appear like an innocuous material on a radiograph. The value of the ratio (average Z/average $Z^2$), however, is independent of the density, making it harder to subvert the system.

Other mathematical combinations of the values may be useful, as well, as is known in the art. The voxel value based on a radiograph at one or both energy levels may also be used in the data analysis.

The images derived from the second, energy sensitive detector array 60, while providing material content information, has low resolution. Corresponding radiograph/CT images derived from data collected by the first detector array 20, which have high resolution, and the images derived from data from the second detector array 60 may also be fused, voxel by voxel, to yield an image with high spatial resolution that also indicates the material content of the voxel. The position, size and shape of suspicious material, as well as the identity of the material, may then be analyzed visually or by the computer 26.

The computer may implement software programs that automatically analyze the images or the image data to identify suspicious objects or materials, as is known in the art. Software may also be used to enhance the displayed image to facilitate visual analysis by an operator. For example, edge enhancement programs may be used, color may be added to identify certain types of materials and surface rendering may be provided, to make objects more recognizable, as is known in the art.

While the invention is particularly suited for scanning cargo containers for contraband, the invention may be readily adapted to scan other objects, as well, such as luggage and carry-on bags in airports.

In addition, while a plurality of sources is shown in FIG. 1, a single source may also be used. The single source may be rapidly moved across the rail 18 by the conveying system 22.

Furthermore, while an X-ray source is described in the examples above, the source or sources may provide other types of radiation, such as a neutron beam, for example.

One of ordinary skill in the art will recognize that other changes may be made to the embodiments described herein without departing from the scope of the invention, which is defined by the claims, below.

We claim:

1. A scanning unit for examining contents of an object movable along a predetermined first path, the scanning unit comprising:
    a rail transverse to the first path;
    one or more sources of respective beams of radiation, at least one of the one or more sources being supported by the rail and being movable across a second path transverse to the first path, along the rail, the second path extending only partially around the first path; and
    a stationary detector extending only partially around the first path, the detector being positioned to detect radiation transmitted through the object during scanning.

2. The scanning unit of claim 1, wherein the object is a cargo container and the detector and the at least one source of radiation are positioned to allow the cargo container to be transported therebetween, along the first path.

3. The scanning unit of claim 2, wherein the cargo container is carried by a vehicle; and
    the detector and the at least one source of radiation are positioned to allow the cargo and the vehicle to be transported therebetween.

4. The scanning unit of claim 1, wherein the detector is located, at least in part, beneath the first path, below ground; and
    the at least one source is located above the first path.

5. The scanning unit of claim 1, wherein the second path is a semi-circle and the at least one of the one or more sources is movable about the semi-circle, the semi-circle lying on an imaginary circle having a center within the object when the object is in a position for scanning.

6. The scanning unit of claim 5, wherein:
    the rail is a semi-circular rail perpendicular to the first path; and
    a plurality of sources are supported by the rail and are movable with respect to the rail along the second path, about the semi-circle.

7. The scanning unit of claim 5, wherein the detector is a detector array comprising a semi-circular row of detectors perpendicular to the first path and lying on an imaginary circle having a center within the object when the object is in a position for scanning.

8. The scanning unit of claim 1, wherein the detector comprises a plurality of two dimensional detectors.

9. The scanning unit of claim 1, comprising at least one energy sensitive detector.

10. The scanning unit of claim 1, wherein the at least one source is a source of X-ray radiation.

11. The scanning unit of claim 1, wherein the beam is a cone beam.

12. The scanning unit of claim 1, further comprising a processor electrically coupled to the detector array, the processor being programmed to reconstruct computed tomography images based on data received from the detector array.

13. The scanning unit of claim 1, further comprising a transport system to convey the object through the scanning unit, along the first path.

14. The scanning unit of claim 1, wherein each of the at least one sources is a linear accelerator.

15. The scanning unit of claim 1, further comprising:
    a transport system to transport an object along the first path.

16. The scanning unit of claim 1, wherein:
    the rail is arcuate; and
    the second path is arcuate.

17. A scanning unit for examining the contents of an object moving along a predetermined first path, the scanning unit comprising:
    one or more sources of X-ray radiation, at least one of the one or more sources being adapted to provide a respective cone beam of X-ray radiation to irradiate the object and each of the at least one sources being mechanically movable across a single, common second path transverse to the first path, the second path extending only partially around the first path; and
    a stationary detector extending only partially around the first path, the detector being positioned to detect radiation after a respective cone beam passes through the object during scanning;
    wherein the second path and the detector extend sufficiently around the object to collect sufficient data for computed tomographic imaging.

18. The scanning unit of claim 17, wherein the object is a cargo container and the X-ray sources and the detector are positioned to allow transport of the cargo container therebetween.

19. The scanning unit of claim 17, further comprising:
    a semi-circular rail supported by the scanning unit perpendicular to the first path,
    the semi-circular rail lying on an imaginary circle having a center within the object when the object is in position for scanning,
    wherein the rail supports the at least one of the one or more sources, the at least one of the one or more sources being movable in a semi-circle about the rail; and
    the detector array is semi-circular,
    is perpendicular to the path, and
    lies on an imaginary circle having a center within the cargo when the cargo is in position for scanning.

20. The scanning unit of claim 17, wherein the detector is a detector array comprising a plurality of rows of detector modules.

21. The scanning unit of claim 17, wherein at least one of the sources emits radiation having a first energy distribution and at least one of the sources emits radiation having a second energy distribution different than the first energy distribution.

22. The scanning unit of claim 21, further comprising a second, energy sensitive, detector,
wherein the first detector is between the second detector and the plurality of sources.

23. The scanning unit of claim 22, further comprising a processor electrically coupled to the first and second detectors, the processor being programmed to:
reconstruct computed tomography images based on data received from the first detector;
reconstruct energy based images based on data received from the second detector; and
fuse the images based on data from the first detector array with the images based on the data received from the second detector.

24. The scanning unit of claim 17, wherein each of the plurality of sources are operational to selectively switch between emitting radiation having a first energy distribution and radiation having a second energy distribution different than the first energy distribution.

25. The scanning unit of claim 24, further comprising a second, energy sensitive, detector,
wherein the first detector is between the second detector and the plurality of sources.

26. The scanning unit of claim 25, further comprising a processor electrically coupled to the first detector, the processor being programmed to:
reconstruct computed tomography images based on data received from the first detector;
reconstruct energy based images based on data received from the second detector; and
fuse the images based on data from the first detector array with the images based on the data received from the second detector array.

27. The scanning unit of claim 17, further comprising a processor electrically connected to the detector, the processor being programmed to reconstruct computed tomography images based on data received from the detector.

28. The scanning unit of claim 17, wherein the cone beam is an asymmetric rectangular cone beam.

29. The scanning unit of claim 17, further comprising:
a transport system to transport the object along the first path.

30. The scanning system of claim 17, wherein:
the source and the detector are positioned to allow passage of a truck therebetween, to scan an object carried by the truck.

31. A cargo scanning unit comprising:
means for transporting a cargo container along a path through the scanning unit;
a semi-circular rail supported by the unit above the path, transverse to the path, the semi-circular rail lying on a first imaginary circle having a center within the cargo container when the cargo is in position for scanning;
a plurality of movable sources of X-ray radiation supported by the rail, each source to provide a cone beam of X-ray radiation; and
a semi-circular detector array having at least a portion below the path, beneath ground level, the detector array being transverse to the path and lying on a second imaginary circle having a center within the cargo container when the cargo container is in position for scanning;
wherein the first and second imaginary circles lie in a same plane; and
the detector array comprises a plurality of two dimensional detectors.

32. The cargo scanning unit of claim 31, wherein the detector array is stationary.

33. The cargo scanning unit of claim 31, wherein at least one of the sources emits radiation having a first energy distribution and at least one of the sources emits radiation having a second energy distribution different than the first energy distribution.

34. The cargo scanning unit of claim 33, further comprising a second, energy sensitive, detector array,
wherein the first detector array is between the second detector array and the plurality of sources.

35. The cargo scanning unit of claim 31, wherein each of the plurality of sources are operational to selectively switch between emitting radiation having a first energy distribution and radiation having a second energy distribution different than the first energy distribution.

36. The cargo scanning unit of claim 35, further comprising a second, energy sensitive, detector array,
wherein the first detector array is between the second detector array and the plurality of sources.

37. The cargo scanning unit of claim 31, wherein the X-ray sources are linear accelerators having acceleration potentials greater than about 1 MV.

38. The cargo scanning unit of claim 31, wherein the cone beam covers an angle of about 20 to about 30 degrees.

39. A method of examining contents of a cargo container, comprising:
moving at least one source of radiation along a single, common arc extending only partially around a cargo container;
scanning at least a portion of the cargo container with at least one respective radiation beam from the at least one source of radiation at a plurality of angles;
detecting radiation from the at least one source, transmitted through the cargo container; and
processing data based on the radiation detected from the at least one source moved along the single arc, to form computed tomographic images of at least the portion of the cargo container.

40. The method of claim 39, further comprising:
moving the cargo container along a path in a first direction;
scanning at least a portion of the cargo container by a plurality of radiation beams, each scanning the cargo container at a different angle; and
detecting radiation transmitted through the cargo container by a stationary detector.

41. The method of claim 40, further comprising:
moving a source of the radiation beam in a second direction transverse to the first direction to scan the cargo container; and
detecting radiation transmitted through the cargo container by a stationary detector.

42. The method of claim 39, comprising scanning the cargo container with a cone beam of radiation.

43. The method of claim 39, comprising scanning the cargo container with X-ray radiation.

44. The method of claim 39, comprising scanning the cargo container with a radiation beam having a first energy distribution and scanning the cargo container with a radiation beam having a second energy distribution different from the first energy distribution.

45. The method of claim 44, comprising:
detecting radiation with a first, spatial detector;
detecting radiation with a second, energy sensitive, detector; and
processing data based on the detected radiation from the first and second detectors to form respective computed tomographic images of the cargo container.

46. The method of claim 45, comprising:
fusing corresponding computed tomographic images from the radiation detected from the first and second detectors.

47. The method of claim 39, further comprising: first;
scanning the entire cargo container with a beam of radiation,
producing radiographs of the cargo container, and
identifying suspicious regions of the cargo container based on the radiographs, and then;
scanning the suspicious regions of the cargo container with a radiation beam at the plurality of angles,
detecting radiation transmitted through the cargo container, and
processing data based on the detected radiation to form computed tomographic images of the suspicious regions of the cargo container.

48. The method of claim 47, comprising scanning the entire cargo container with a pencil beam of radiation.

49. The method of claim 39, comprising scanning a cargo container having a height and/or width of at least about 1.5 meters.

50. The method of claim 39, comprising:
mechanically moving the at least one source of radiation along an arcuate rail.

51. The method of claim 39, wherein the cargo container is supported by a truck, the method further comprising:
moving the truck and the cargo container between the at least one source and the detector during scanning.

52. A method of examining contents of an object, comprising:
moving the object along a first path;
moving at least one source of a radiation beam along a second path transverse to the first path, along a rail, to scan the object, the second path extending only partially around the first path; and
detecting radiation transmitted through the object by a stationary detector array, the detector array extending only partially around the first path.

53. The method of claim 52, comprising reconstructing images based on the detected radiation.

54. The method of claim 53, comprising reconstructing computed tomography images based on the detected radiation.

55. The method of claim 52, comprising:
irradiating the object with a first radiation beam having a first energy distribution; and
irradiating the object with a second radiation beam having a second energy distribution different from the first energy distribution.

56. The method of claim 55, comprising:
detecting radiation transmitted through the object with a first, spatial detector array; and
detecting radiation transmitted through the object with a second, energy sensitive, detector.

57. The method of claim 56, comprising:
reconstructing computed tomography images from the radiation detected by the first detector;
reconstructing images from the radiation detected by the second detector; and
fusing corresponding images from the radiation detected from the first and second detectors.

58. The method of claim 56, comprising:
detecting radiation from the first radiation beam transmitted through the object;
detecting radiation from the second radiation beam transmitted through the object;
computing a first value based on the detected radiation from the first radiation beam, for a plurality of voxels of the object;
computing a second value based on the detected radiation from the second radiation beam, for the plurality of voxels of the object;
processing the first and second values for the plurality of voxels; and
determining a material content of the plurality of voxels based on the processing.

59. The method of 58, comprising;
processing the first and second values by computing a ratio of the first and second values for the plurality of voxels; and
determining the material content of the plurality of voxels based on the ratio.

60. The method of claim 52, further comprising:
identifying suspicious regions of the object; then
irradiating the suspicious regions at a plurality of angles with a radiation beam from the at least one moving source;
detecting radiation caused by the interaction of the suspicious regions with the radiation beam; and
reconstructing computed tomography images of the suspicious regions from the detected radiation.

61. The method of claim 52, comprising moving a cargo container along the first path.

62. The method of claim 61, comprising supporting the cargo container on a truck.

63. The method of claim 52, further comprising generating a cone beam to scan the object.

64. The method of claim 52, comprising:
moving the at least one source along a semi-circular second path along a semi-circular rail.

65. A scanning unit for examining a target movable along a predetermined first path, the scanning unit comprising:
a rail transverse to the first path;
a plurality of sources of beams of radiation supported by and movable across a second path transverse to the first path, along the rail; and
a detector positioned to detect radiation transmitted through a target during scanning.

66. The scanning unit of claim 65, wherein the second path extends partially around the first path, along the rail.

67. The scanning unit of claim 65, wherein the detector extends only partially around the first path.

68. The scanning unit of claim 65, wherein the detector is stationary.

69. The scanning unit of claim 65, wherein the plurality of sources are sources of X-ray radiation.

70. The scanning unit of claim 65, further comprising:
a transport system to transport the target along the first path.

71. The scanning unit of claim 65, wherein:
at least one of the plurality of sources generates radiation having an energy of at least 1 MeV.

72. The scanning unit of claim 65, further comprising:
means for transporting a cargo container along the first path;
wherein the plurality of sources and the detector are positioned so that the means for transporting can transport a cargo container along the first path, between the at least one of the one or more sources and the detector.

73. A scanning unit for examining an object, the scanning unit comprising:
means for transporting an object along a first path;
an arcuate rail transverse to the path;
one or more sources of radiation to irradiate the object, at least one of the one or more sources generating radiation having an energy of at least 1 MeV, being supported by the arcuate rail and being movable over at least a portion of a second path transverse to and only partially around the first path, along the rail;
a detector positioned to detect radiation transmitted through the object; and
a processor to reconstruct computed tomographic images based on the data collected by the detector, from radiation generated by the at least one of the one or more sources.

74. The scanning unit of claim 73, wherein:
the at least one of the one or more sources is mechanically movable over the at least a portion of the second path.

75. The scanning unit of claim 73, wherein:
the detector is stationary.

76. The scanning unit of claim 73, wherein:
the means for transporting is a means for transporting a cargo container; and
the at least one of the one or more sources and the detector are positioned so that the means for transporting can transport a cargo container along the first path between the at least one of the one or more sources and the detector.

77. The scanning unit of claim 73, wherein:
the arcuate rail is semi-circular; and
the second path is semi-circular.

78. A scanning unit for examining an object, the scanning unit comprising:
means for transporting an object along a first path;
an arcuate rail transverse to the first path;
one or more sources of radiation to irradiate the object, at least one of the one or more sources being mechanically movable over at least a portion of a second path transverse to the first path, along the arcuate rail, to irradiate the object; and
a detector positioned to detect radiation after interaction with the object, the detector extending only partially around the first path.

79. The scanning unit of claim 78, wherein the detector is stationary.

80. A scanning unit for examining an object, the scanning unit comprising:
means for transporting the object along a first path;
a semi-circular rail transverse to the first path;
a plurality of radiation sources to irradiate the object, at least two of the plurality of radiation sources being self-contained sources, each of the self-contained sources being movable over a portion of a second path, along the semi-circular rail; and
a detector positioned to detect radiation transmitted through the object during scanning.

81. The scanning unit of claim 80, wherein:
the self-contained radiation sources are chosen from a group consisting of a linear accelerator, an electrostatic accelerator, a microtron, a betatron, and an X-ray tube.

82. The scanning unit of claim 80, wherein each of the self-contained sources generate radiation of at least 1 MeV.

83. The scanning unit of claim 80, wherein the detector is stationary.

84. The scanning unit of claim 80, wherein:
the means for transporting is a means for transporting a cargo container; and
the at least one of the one or more sources and the detector are positioned so that the means for transporting can transport a cargo container along the first path, between the at least one of the one or more sources and the detector.

85. A scanning unit for examining a cargo container, the scanning unit comprising:
means for transporting a cargo container along a first path; and
one or more sources of radiation to irradiate the cargo container, at least one of the one or more sources being adapted to irradiate the cargo container with a cone beam of radiation, each of the at least one source of a cone beam of radiation being movable over a single, second path transverse to and at least partially around the first path; and
a stationary detector positioned to detect the cone beam of radiation after interaction with the cargo container;
wherein the at least one of the one or more sources and the detector are positioned so that the means for transporting can transport the cargo container along the first path, between the at least one of the one or more sources and the detector.

86. A scanning unit for examining contents of a cargo container, the scanning unit comprising:
means for transporting a cargo container through the system, along a first path;
an arcuate rail transverse to the first path;
one or more sources of radiation to irradiate the cargo container, at least one of the one or more sources being movable over a second path transverse to and only partially around the first path, along the rail; and
a detector positioned to detect radiation transmitted through the cargo container by the at least one of the one or more sources, to collect sufficient data for computed tomographic reconstruction;
wherein the at least one of the one or more sources and the detector are positioned so that the means for transporting can transport a cargo container between the at least one of the one or more sources and the detector.

87. The scanning unit of claim 86, wherein:
the at least one of the one or more sources generates radiation of at least 1 MeV.

88. The scanning unit of claim 86, wherein the at least one of the one or more sources are each linear accelerators.

89. The scanning unit of claim 86, wherein the at least one of the one or more sources generates a cone beam of radiation with which to irradiate the cargo container.

90. The scanning unit of claim 86, wherein:
the path extends over an arc of at least 180 degrees; and
the detector extends over an arc of at least 180 degrees.

91. The scanning unit of claim 86, wherein:
the at least one of the one or more sources emits a radiation beam having a lateral arc parallel to the second path;

the second path is arcuate;

the detector is arcuate; and at least either the second path or the detector extends over an arc of at least 180 degrees plus the lateral arc of the radiation beam emitted by the at least one of the one or more sources, to obtain a complete data set for computed tomographic reconstruction.

92. The scanning unit of claim 86, wherein the detector is stationary.

93. The scanning unit of claim 86, wherein:

the at least one of the one or more sources is mechanically movable over the at least a portion of the second path.

94. The scanning unit of claim 86, wherein the cargo container has a height and/or width of at least 1.5 meters.

95. A method of examining contents of a cargo container, comprising:

providing one or more sources of radiation;

moving at least one of the one or more sources of radiation over at least a portion of a path extending only partially around a cargo container, along an arcuate rail;

scanning at least a portion of the cargo container with radiation from the at least one source;

detecting radiation transmitted through the cargo container, the detected radiation comprising sufficient data for computed tomographic reconstruction of at least a portion of the contents of the cargo container; and processing data based on the detected radiation to form computed tomographic images of at least the portion of the contents of the cargo container based on the data.

* * * * *